(12) United States Patent
Muggleton et al.

(10) Patent No.: US 10,390,157 B2
(45) Date of Patent: Aug. 20, 2019

(54) HEARING PROTECTION DEVICE SELF-ASSESSMENT OF SUITABILITY AND EFFECTIVENESS TO PROVIDE OPTIMUM PROTECTION IN A HIGH NOISE ENVIRONMENT BASED ON LOCALIZED NOISE SAMPLING AND ANALYSIS

(71) Applicant: Honeywell International Inc., Morris Plains, NJ (US)

(72) Inventors: Neal Anthony Muggleton, Stevenage (GB); Trym Holter, Trondheim (NO)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 0 days.

(21) Appl. No.: 16/104,303

(22) Filed: Aug. 17, 2018

(65) Prior Publication Data

US 2019/0058957 A1 Feb. 21, 2019

Related U.S. Application Data

(60) Provisional application No. 62/547,330, filed on Aug. 18, 2017.

(51) Int. Cl.
| | |
|---|---|
| *H04R 29/00* | (2006.01) |
| *G10L 25/51* | (2013.01) |
| *H04R 3/04* | (2006.01) |
| *H04R 1/10* | (2006.01) |
| *A61F 11/06* | (2006.01) |

(52) U.S. Cl.
CPC .............. *H04R 29/00* (2013.01); *A61F 11/06* (2013.01); *G10L 25/51* (2013.01); *H04R 1/1083* (2013.01); *H04R 3/04* (2013.01); *H04R 2420/07* (2013.01)

(58) Field of Classification Search
None
See application file for complete search history.

(56) References Cited

U.S. PATENT DOCUMENTS

| | | | |
|---|---|---|---|
| 6,826,515 B2* | 11/2004 | Bernardi | G01H 3/14 379/387.01 |
| 10,068,451 B1* | 9/2018 | Werner | G08B 21/02 |
| 2008/0011084 A1* | 1/2008 | Von Dach | G01H 15/00 73/584 |
| 2008/0144842 A1* | 6/2008 | Goldstein | A61B 5/121 381/56 |

(Continued)

FOREIGN PATENT DOCUMENTS

WO 2016168486 A1 10/2016

*Primary Examiner* — Paul W Huber
(74) *Attorney, Agent, or Firm* — Wick Phillips Gould & Martin, LLP

(57) ABSTRACT

Embodiments relate generally to devices, systems, and methods for assessing a hearing protection device. A method for assessing a hearing protection device may comprise monitoring sounds with a hearing protection device; transmitting sound measurements from the hearing protection device to a portable electronic device; transmitting the sound measurements from the portable electronic device to a server; comparing, with the portable electronic device or the server, sound measurements to a look-up table; suggesting, with the portable electronic device, the most suitable hearing protection device to be worn based on a comparison between the sound measurements and the look-up table.

18 Claims, 1 Drawing Sheet

(56) References Cited

U.S. PATENT DOCUMENTS

| | | | | |
|---|---|---|---|---|
| 2008/0205660 A1* | 8/2008 | Goldstein | ............ | A61B 5/0002 |
| | | | | 381/60 |
| 2010/0135502 A1* | 6/2010 | Keady | ................... | A61B 5/121 |
| | | | | 381/58 |
| 2012/0321094 A1* | 12/2012 | Schiller | ................... | G01H 3/14 |
| | | | | 381/56 |
| 2013/0259241 A1* | 10/2013 | Schul | ..................... | H04R 3/002 |
| | | | | 381/56 |
| 2015/0010158 A1* | 1/2015 | Broadley | ............... | H04R 29/00 |
| | | | | 381/58 |
| 2016/0316306 A1* | 10/2016 | Nooralahiyan | ......... | G06F 3/162 |
| 2017/0188166 A1* | 6/2017 | Eberbach | ................ | H04R 29/00 |
| 2017/0372216 A1* | 12/2017 | Awiszus | ................ | G06N 7/005 |

* cited by examiner

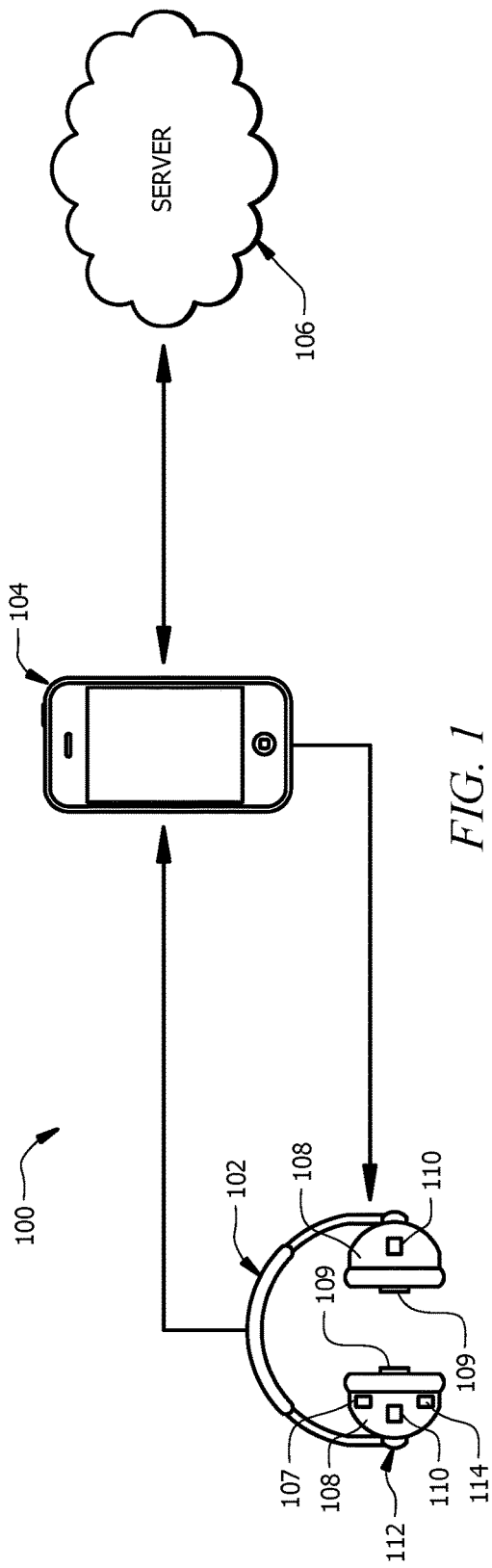

HEARING PROTECTION DEVICE SELF-ASSESSMENT OF SUITABILITY AND EFFECTIVENESS TO PROVIDE OPTIMUM PROTECTION IN A HIGH NOISE ENVIRONMENT BASED ON LOCALIZED NOISE SAMPLING AND ANALYSIS

CROSS-REFERENCE TO RELATED APPLICATIONS

The present application claims priority to U.S. Provisional Patent Application Ser. No. 62/547,330 filed Aug. 18, 2017 by Neal Anthony Muggleton, et al. and entitled "Hearing Protection Device Self-Assessment of Suitability and Effectiveness to Provide Optimum Protection in a High Noise Environment Based on Localized Noise Sampling and Analysis" which is incorporated herein by reference as if reproduced in its entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Some environments are noisy due to industrial equipment. The noise from this equipment can cause permanent hearing damage to workers if protection is not provided. To reduce the noise level in these types of environments to a safe level, hearing protection devices ("HPDs"), such as, for example, ear muffs or ear plugs may be utilized.

SUMMARY

In an embodiment, a system for assessing a hearing protection device may comprise the hearing protection device; a portable electronic device; and a server; wherein the server is wirelessly coupled to the portable electronic device; wherein the portable electronic device is wirelessly coupled to the hearing protection device; wherein the hearing protection device is configured to monitor sounds and transmit sound measurements to the portable electronic device and/or the server.

In an embodiment, a method for assessing a hearing protection device may comprise monitoring sounds with a hearing protection device; transmitting sound measurements from the hearing protection device to a portable electronic device; transmitting the sound measurements from the portable electronic device to a server; comparing, with the portable electronic device or the server, sound measurements as a function of frequency to a look-up table; suggesting, with the portable electronic device, the most suitable HPD to be worn based on a comparison between the sound measurements and the look-up table.

In an embodiment, a system for assessing a hearing protection device may comprise the hearing protection device; a portable electronic device; and a server; wherein the server and the portable electronic device are configured to perform the sound measurements in octave bands; wherein the portable electronic device and the server are configured to compare sound measurements to an octave band look-up table.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

FIG. 1 is a schematic illustration of a system for filtering sound in accordance with embodiments of the disclosure.

FIG. 2 illustrates a look-up table of hearing protection devices ("HPD") and their corresponding HML rating(s) in accordance with embodiments of the disclosure.

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field (for example ±10%); and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

A-Weighting (dBA) may be a filter applied by noise measurement devices, intended to replicate frequency sensitivity of a human ear. Sound level meters set to the A-weighting may filter out low-frequency noise they measure, similar to the response of the human ear.

C-Weighting (dBC) may be a filter applied to noise measurements. In contrast to the A-weighting, the C-weighting is a "flatter" filter, and may allow low frequencies to be measured.

The High-Medium-Low ("HML") calculation technique may provide an accurate measurement of hearing protection device performance. The first number (H) may represent attenuation in high-frequency environments (e.g., frequencies within approximately 2 to 8 kilohertz (kHz)), the middle number (M) may represent attenuation in medium frequency environments (e.g., frequencies within approximately 1 to 2 kHz), and the third number (L) may represent attenuation in low frequency environments (e.g., frequencies within approximately 63 hertz to 1 KHz). These ranges may be examples, where other frequencies may be included in the high, medium, and/or low frequency environments. An advantage of HML calculations (HML rating(s)) may be that only dBA and dBC are required as noise data input.

Hearing Protection Devices ("HPDs") may all work differently under different noise conditions. HPD attenuation characteristics are generally not flat, therefore the noise attenuation provided may vary based on the different frequencies of noise present in the environment.

The universally used noise reduction rating ("NRR")/single number rating ("SNR") attenuation figures may provide an indication of the attenuation level that might be achieved, but do not reflect attenuation performance in different parts of the frequency range.

A more accurate approach may be to use the High Medium Low ("HML") rating for the HPD (e.g., a headset) and match the more accurate performance characteristics of the HPD against the noise environment (e.g., frequency spectrum of noise) measured by the actual HPD when it is being used.

Embodiments of the disclosure may relate to sound level and frequency based analysis for selecting appropriate hearing protection, which may include analysis in an HPD (e.g., via outer and inner microphones), and recordings in the HPD and analysis elsewhere (e.g., via outer and inner microphones), where analysis/recording may not be continuous, but be short term (e.g., 2-3 seconds) and triggered by events (e.g., high noise conditions, typical noise conditions). Sampling and averaging of noise may be performed throughout a work day, and recommendations may be given based on the sound level and frequency analysis to help keep a user safe, and to help keep the user comfortable (e.g., by suggesting that what he is using is overkill, where excessive protection may isolate employees from important communications, including co-workers' voices, machine sounds, alarms and signals). For example, a worker who cannot hear a warning signal of a piece of equipment can be in serious danger. Also, a worker who cannot hear on the job may be more likely to make mistakes than a worker who can communicate clearly with others. In some embodiments, the recommendations may result in the dispensation of appropriate hearing protection, either with increased or decreased hearing protection levels. In some embodiments, the recommendations may be communicated to (and/or created by) a work station and/or kiosk which may be configured to dispense/provide the appropriate hearing protection device based on the recommendations. In other words, a kiosk may be configured to complete the sampling and averaging of noise, generation of recommendations, and dispensation of appropriate hearing protection based on the generated recommendations.

Analysis techniques (e.g., performed in the HPD) may include calculating/providing A-filtered sound levels (dBA) and C-filtered sound levels (dBC). Embodiments may also include utilizing a non-standard filter bank (e.g., only a few frequency bands, for example, to approximate HML); an octave band filter bank; an octave band analysis based on Fast Fourier Transform ("FFT"). Embodiments may also reuse functionality needed, for example, for dose measurement and/or hear-through optimization. If run on an external device (e.g., smart phone/tablet/personal computer ("PC")/cloud) based on recordings, the octave band analysis based on FFT may be utilized.

HPD may perform an octave band analysis to determine the noise spectrum and then may perform a look up into a table (e.g., a database) of other personal protection equipment ("PPE")/HPDs (e.g., plugs and muffs). PPE may include HPD. The table of other HPDs could be filtered (e.g., by only those approved and available, such as, by employees of a company); or the look-up table could be a cloud service that may be constantly updated with an industry wide database. The HPD may continuously compare the noise with an optimum/recommended HPD and alert the worker if a more appropriate device should be used; or the HPD may indicate to the worker that an alternative HPD/PPE (i.e., used with the same noise environment) would reduce the total noise exposure and personal risk of noise induced hearing loss ("NIHL").

FIG. 1 is a schematic illustration of system 100 for monitoring environmental sounds. System 100 may include hearing protection device ("HPD") 102, portable electronic device 104 (e.g., smart phone, tablet, or personal computer ("PC")), and server 106 (e.g., a cloud based server). Portable electronic device 104 and server 106 may each include a transceiver for communication. HPD 102 may be wirelessly coupled to portable electronic device 104, and server 106 may be wirelessly coupled to portable electronic device 104. Server 106 and portable electronic device 104 may communicate with each other. HPD 102 and portable electronic device 104 may communicate with each other.

HPD 102 may include a processing system 107 (e.g., memory and processor) and include ear cups 108. Each ear cup 108 may include externally facing microphone 110. At least one ear cup 108 may include an externally facing button 112 for a user interface/confirmation, and transceiver 114. Each ear cup 108 may include a speaker 109 for transmitting auditory messages to a user of HPD 102. In certain embodiments, HPD 102 may include earbuds (with externally facing microphones) which may be inserted into an ear canal. HPD 102 may monitor/receive sounds (e.g., sound measurements) of the environment through microphones 110. In certain embodiments, HPD 102 may monitor sounds for about 2 seconds to about 3 seconds (e.g., sampling of noise may be about 2 seconds to about 3 seconds). Processing system 107 may filter the sound measurements according to standard algorithms/practices to provide/calculate weighted A (dBA) and C (dBC). For example, standard algorithms/practices may include, but are not limited to, ITU-R 468, ITU-R BS.468-4, and/or IEC 61672:2003. In some embodiments, portable electronic device 104 and/or server 106 may process and/or filter the sound measurements.

In certain embodiments, HPD 102 may transmit the sound measurements to portable electronic device 104 for processing (e.g., filtering) via an app. In other embodiments, HPD 102 may transmit the sound measurements to portable electronic device 104; portable electronic device 104 may receive these sound measurements and then transmit the sound measurements to server 106 for processing. Sound measurements may be processed/filtered via an octave band analysis which may filter sound signals with an octave band filter bank. The octave band filter bank may be included/stored in HPD 102, portable electronic device 104, and/or server 106. The octave band analysis may be based on Fast Fourier Transform. HPD 102, portable electronic device 104, and/or server 106 may compare these sound measurements to an HML/PPE look-up table 116 ("look-up table 116") (shown on FIG. 2) to indicate a suitable/optimal PPE to be worn in the work environment based on the sound measurements. That is, look-up table 116 may include HPD and the HPD's corresponding HML ratings.

Portable electronic device 104 and/or server 106 may create/provide a suggestion as to which HPD would perform optimally in the work environment based on the comparison of the sound measurements to the stored information/values within look-up table 116, as noted above. That is, if the difference between the measured values (e.g., sound measurements) and the HML ratings exceeds a threshold, then the suggestion may recommend using one piece of HPD; if the difference is within the threshold, then the suggestion may recommend using another or different piece/type of HPD. This suggestion may be transmitted from server 106 to portable electronic device 104; portable electronic device 104 may then transmit this suggestion to HPD 102. HPD 102 may relay/transmit this suggestion to a user as an auditory message via speakers 109. If portable electronic device 104 creates/provides the suggestion, portable electronic device 104 may directly transmit the suggestion to HPD 102. In some embodiments, the suggestion may also be communicated to a kiosk and/or work station, where the appropriate HPD may be dispense or otherwise acquired by the user.

Based on the processed/analyzed sound measurements, HPD 102, portable electronic device 104, and/or server 106 may also indicate, via an auditory message, a sound exposure a user is exposed to while wearing HPD for each piece/type of HPD. Also, HPD 102, portable electronic device 104, and/or server 106 may indicate, via an auditory message, a difference in sound exposure (i.e., how much better or worse a user's sound exposure could have been if the user were to wear a different piece/type of HPD, and/or a difference in sound exposure between different pieces/types of HPD).

Devices, systems, and/or methods of the disclosure may be implemented by an information handling system (e.g., HPD 102, portable electronic device 104, and/or server 106 may each include an information handling system). For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer or tablet device, a cellular telephone, a network storage device, or any other suitable device and may vary in size, shape, performance, functionality, and price. The information handling system may include a transceiver, random access memory ("RAM"), one or more processing resources such as a central processing unit ("CPU") or hardware or software control logic, read-only memory ("ROM"), and/or other types of nonvolatile memory. Additional components of the information handling system may include one or more disk drives, one or more network ports for communication with external devices as well as various input and output (I/O) devices, such as a keyboard, a mouse, and a video display. The information handling system also may include one or more buses operable to transmit communications between the various hardware components.

The information handling system may also include computer-readable media. Computer-readable media may include any instrumentality or aggregation of instrumentalities that may retain data and/or instructions for a period of time. Computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory ("EEPROM"), and/or flash memory; as well as communications media such as wires, optical fibers, microwaves, radio waves, and other electromagnetic and/or optical carriers; and/or any combination of the foregoing.

Having described various systems and methods, various embodiments can include, but are not limited to:

In a first embodiment, a system for assessing a hearing protection device may comprise the hearing protection device; a portable electronic device; and a server; wherein the server is wirelessly coupled to the portable electronic device; wherein the portable electronic device is wirelessly coupled to the hearing protection device; wherein the hearing protection device is configured to monitor sounds and transmit sound measurements to the portable electronic device and/or the server.

A second embodiment may include the system of the first embodiment, wherein the hearing protection device, the portable electronic device, and the server are configured to calculate an A-weighted noise measurement (dBA) and a C-weighted noise measurement (dBC).

A third embodiment may include the system of the first or second embodiment, wherein the hearing protection device, the portable electronic device, and the server are configured to indicate a sound exposure.

A fourth embodiment may include the system of any of the preceding embodiments, wherein the hearing protection device, the portable electronic device, and the server are configured to indicate a difference in sound exposure between different HPD.

A fifth embodiment may include the system of any of the preceding embodiments, wherein the server and the portable electronic device are configured to filter sound measurements with an octave band filter bank.

A sixth embodiment may include the system of any of the preceding embodiments, wherein the octave band filter bank is based on a Fast Fourier Transform.

A seventh embodiment may include the system of any of the preceding embodiments, wherein the portable electronic device and/or the server include a look-up table comprising high, medium, low frequency (HML) ratings and corresponding HPD.

An eighth embodiment may include the system of any of the preceding embodiments, wherein the portable electronic device and the server are configured to compare filtered sound measurements to the look-up table.

A ninth embodiment may include the system of any of the preceding embodiments, wherein the portable electronic device and the server are configured to provide a suggestion based on a comparison between the filtered sound measurements and the look-up table, wherein the suggestion comprises HPD to be worn.

A tenth embodiment may include the system of any of the preceding embodiments, wherein the hearing protection device is configured to sample noise for about 2 seconds to about 3 seconds.

In an eleventh embodiment, a method for assessing a hearing protection device may comprise monitoring sounds with a hearing protection device; transmitting sound measurements from the hearing protection device to a portable electronic device; transmitting the sound measurements from the portable electronic device to a server; comparing, with the portable electronic device or the server, sound measurements to a look-up table; suggesting, with the portable electronic device, HPD to be worn based on a comparison between the sound measurements and the look-up table.

A twelfth embodiment may include the method of the eleventh embodiment, further comprising transmitting a suggestion from the portable electronic device to the hearing protection device.

A thirteenth embodiment may include the method of the eleventh or twelfth embodiments, further comprising calculating A-weighted noise measurement (dBA) and C-weighted noise measurement (dBC) with the hearing protection device, the portable electronic device, or the server.

A fourteenth embodiment may include the method of any one of the eleventh through thirteenth embodiments, further comprising sampling noise, with the hearing protection device, for about 2 seconds to about 3 seconds.

A fifteenth embodiment may include the method of any one of the eleventh through fourteenth embodiments, further comprising filtering the sound measurements with the octave band filter bank.

In a sixteenth embodiment, a system for assessing a hearing protection device may comprise the hearing protection device; a portable electronic device; and a server; wherein the server and the portable electronic device are configured to filter sound measurements with an octave band filter bank; wherein the portable electronic device and the server are configured to compare filtered sound measurements to a look-up table.

A seventeenth embodiment may include the system of the sixteenth embodiment, wherein the portable electronic device and the server are configured to provide a suggestion based on a comparison between the filtered sound measurements and the look-up table.

An eighteenth embodiment may include the system of the sixteenth or seventeenth embodiment, wherein the hearing protection device, the portable electronic device, and the server are configured to calculate an A-weighted noise measurement (dBA) and a C-weighted noise measurement (dBC).

A nineteenth embodiment may include the system of any one of the sixteenth through eighteenth embodiments, wherein the hearing protection device is configured to sample noise for about 2 seconds to about 3 seconds.

A twentieth embodiment may include the system of any one of the sixteenth through nineteenth embodiments, wherein the octave band filter bank is based on a Fast Fourier Transform.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A system for assessing a hearing protection device, the system comprising:
   the hearing protection device;
   a portable electronic device wirelessly coupled to the hearing protection device; and a server wirelessly coupled to the portable electronic device;

wherein the hearing protection device is configured to monitor environmental sounds and transmit environmental sound measurements to at least one of the portable electronic device and the server, and wherein either the portable electronic device or the server is configured to compare the environmental sound measurements to a look-up table and suggest one or more hearing protection devices to be worn based on a comparison between the environmental sound measurements and the look-up table.

2. The system of claim 1, wherein the hearing protection device, the portable electronic device, and the server are configured to calculate an A-weighted sound measurement (dBA) and a C-weighted sound measurement (dBC).

3. The system of claim 1, wherein the hearing protection device, the portable electronic device, and the server are configured to indicate a sound exposure.

4. The system of claim 1, wherein the hearing protection device, the portable electronic device, and the server are configured to indicate a difference in sound exposure between different hearing protection devices.

5. The system of claim 1, wherein the server and the portable electronic device are configured to filter sound measurements with an octave band filter bank.

6. The system of claim 5, wherein the octave band filter bank is based on a Fast Fourier Transform.

7. The system of claim 1, wherein the look-up table comprises high, medium, low frequency ratings and corresponding personal protection equipment.

8. The system of claim 7, wherein the portable electronic device and the server are configured to compare filtered sound measurements to the look-up table.

9. The system of claim 1, wherein the hearing protection device is configured to sample noise for about 2 seconds to about 3 seconds.

10. A method for assessing a hearing protection device, the method comprising:

monitoring environmental sounds with a hearing protection device;

transmitting environmental sound measurements from the hearing protection device to a portable electronic device;

transmitting the environmental sound measurements from the portable electronic device to a server;

comparing, with the portable electronic device or the server, the environmental sound measurements to a look-up table; and suggesting, with the portable electronic device, one or more hearing protection devices to be worn based on a comparison between the environmental sound measurements and the look-up table.

11. The method of claim 10, further comprising transmitting a suggestion from the portable electronic device to the hearing protection device.

12. The method of claim 10, further comprising calculating A-weighted noise measurement (dBA) and C-weighted noise measurement (dBC) with at least one of the hearing protection device, the portable electronic device, and the server.

13. The method of claim 10, further comprising sampling noise, with the hearing protection device, for about 2 seconds to about 3 seconds.

14. The method of claim 10, further comprising filtering the sound measurements with an octave band filter bank.

15. A system for assessing a hearing protection device, the system comprising:

the hearing protection device, wherein the hearing protection device is configured to monitor environmental sounds and transmit environmental sound measurements to at least one of the portable electronic device and the server, a portable electronic device; and a server;

wherein the server and the portable electronic device are configured to filter sound measurements with an octave band filter bank; and wherein the portable electronic device and the server are configured to compare filtered sound measurements to a look-up table and suggest one or more hearing protection devices to be worn based on a comparison between the environmental sound measurements and the look-up table.

16. The system of claim 15, wherein the hearing protection device, the portable electronic device, and the server are configured to calculate an A-weighted noise measurement (dBA) and a C-weighted noise measurement (dBC).

17. The system of claim 15, wherein the hearing protection device is configured to sample noise for about 2 seconds to about 3 seconds.

18. The system of claim 15, wherein the octave band filter bank is based on a Fast Fourier Transform.

* * * * *